US008603983B2

(12) United States Patent
Blumenfeld

(10) Patent No.: US 8,603,983 B2
(45) **Date of Patent: *Dec. 10, 2013**

(54) TARGETED DELIVERY OF BOTULINUM TOXIN FOR THE TREATMENT AND PREVENTION OF TRIGEMINAL AUTONOMIC CEPHALGIAS, MIGRAINE AND VASCULAR CONDITIONS

(75) Inventor: Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/474,490

(22) Filed: May 17, 2012

(65) Prior Publication Data

US 2012/0245096 A1 Sep. 27, 2012

Related U.S. Application Data

(63) Continuation of application No. 12/642,545, filed on Dec. 18, 2009, now Pat. No. 8,241,641, which is a continuation of application No. 11/296,079, filed on Dec. 7, 2005, now Pat. No. 7,655,244.

(60) Provisional application No. 60/593,641, filed on Feb. 1, 2005.

(51) Int. Cl.

| | |
|---|---|
| *A61K 38/16* | (2006.01) |
| *A61P 25/06* | (2006.01) |
| *A61P 25/04* | (2006.01) |

(52) U.S. Cl.
USPC ......... 514/18.3; 530/350; 424/9.2; 424/239.1

(58) Field of Classification Search
USPC ............. 424/239.1, 236.1, 9.1, 9.2; 514/18.3; 530/350
See application file for complete search history.

(56) References Cited

U.S. PATENT DOCUMENTS

| | | | | |
|---|---|---|---|---|
| 5,437,291 | A | 8/1995 | Pasricha et al. | |
| 5,670,484 | A | 9/1997 | Binder | |
| 5,714,468 | A | 2/1998 | Binder | |
| 5,766,605 | A | 6/1998 | Sanders et al. | |
| 5,989,545 | A | 11/1999 | Foster et al. | |
| 6,063,768 | A | 5/2000 | First | |
| 6,139,845 | A | 10/2000 | Donovan | |
| 6,299,893 | B1 | 10/2001 | Schwartz et al. | |
| 6,306,423 | B1 | 10/2001 | Donovan et al. | |
| 6,312,708 | B1 | 11/2001 | Donovan | |
| 6,358,917 | B1 | 3/2002 | Carruthers et al. | |
| 6,423,319 | B1 | 7/2002 | Brooks et al. | |
| 6,447,787 | B1 | 9/2002 | Gassner et al. | |
| 6,458,365 | B1 | 10/2002 | Aoki et al. | |
| 6,464,986 | B1 | 10/2002 | Aoki et al. | |
| 6,623,742 | B2 | 9/2003 | Voet | |
| 6,838,434 | B2 | 1/2005 | Voet | |
| 7,172,763 | B2 | 2/2007 | Aoki | |
| 7,270,287 | B2 | 9/2007 | First | |
| 7,361,358 | B2 | 4/2008 | Aoki et al. | |
| 7,393,537 | B2 | 7/2008 | Ackerman | |
| 7,655,244 | B2 | 2/2010 | Blumenfeld | |
| 7,704,511 | B2 | 4/2010 | Turkel | |
| 8,241,641 | B2 * | 8/2012 | Blumenfeld | 424/239.1 |
| 2003/0224019 | A1 | 12/2003 | O'Brien | |
| 2004/0009180 | A1 | 1/2004 | Donovan | |
| 2004/0247606 | A1 | 12/2004 | Borodic et al. | |
| 2005/0123567 | A1 | 6/2005 | First | |
| 2005/0191320 | A1 | 9/2005 | Turkel et al. | |
| 2005/0191321 | A1 | 9/2005 | Turkel et al. | |
| 2006/0104995 | A1 | 5/2006 | Turkel et al. | |
| 2008/0057084 | A1 | 3/2008 | Burstein et al. | |
| 2009/0252764 | A1 | 10/2009 | Blumenfeld | |
| 2012/0040911 | A1 * | 2/2012 | Blumenfeld | 514/18.3 |

FOREIGN PATENT DOCUMENTS

| | | |
|---|---|---|
| DE | 101 50 415 A1 | 5/2003 |
| WO | WO 95/30431 | 11/1995 |
| WO | WO 03/011333 | 2/2003 |
| WO | WO 2004/078201 | 9/2004 |
| WO | WO 2006/083455 | 8/2006 |

OTHER PUBLICATIONS

Agur, A.M.R. and Dailey II, A.F., (2005) Atlas of Anatomy, 11th Ed., Lippincott Williams & Wilkins, Philadelphia, pp. 316, 317, 600, 601, 736.
Aoki K., et al, Mechanisms of the antinociceptive effect of subcutaneous Botox: Inhibition of peripheral and central nociceptive processing, Cephalalgia Sep. 2003;23(7):649.
Aoki K., Evidence for antinociceptive activity of Botulinum toxin type A in pain management. Headache 2003;43 Suppl 1:S9-15.
Aoki K., Pharmacology and immunology of Botulinum toxin serotypes. J Neurol 2001;248 Suppl 1:1/3-1/10.
Aoki, Current Medicinal Chemistry, 11:3085-3092, 2004.

(Continued)

*Primary Examiner* — Chih-Min Kam
(74) *Attorney, Agent, or Firm* — Brigitte C. Phan; Ted Chan; Debra Condino

(57) ABSTRACT

Botulinum toxin, among other presynaptic neurotoxins is used for the treatment and prevention of migraine and other headaches associated with vascular disorders. Presynaptic neurotoxins are delivered focally, targeting the nerve endings of the trigeminal nerve, the occipital nerve and the intranasal terminals of the parasympathetic fibers originating in the Sphenopalatine ganglion. The administration preferably targets the extracranial nerve endings of the trigeminal nerve in the temporal area, the extracranial occipital nerve endings in the occipital area, and the intranasal terminals of the trigeminal nerve and parasympathetic fibers originating in the Sphenopalatine ganglion. The delivery is carried out by way of injection or topically.

3 Claims, 4 Drawing Sheets

(56) References Cited

OTHER PUBLICATIONS

Aoki, K.; et al., Botulinum toxin type A and other Botulinum toxin serotypes: a comparative review of biochemical and pharmacological actions, Eur J. Neurol 2001: (suppl 5); 21-29.
Aoki, K., Physiology and pharmacology of therapeutic Botulinum neurotoxins, in Kreyden, 0., editor, Hyperhydrosis and Botulinum toxin in dermatology, Basel, Karger; 2002; 30: pp. 107-116, at 109-110.
Bhattacharya K., et al., Novel uses of Botulinum toxin type A: two case reports, Mov Disord 2000; 15(Suppl 2):51-52.
Bigal ME, Sheftell FD, Rapoport AM, et al. Chronic daily headache in a tertiary care population: correlation between International Headache Society diagnostic criteria and proposed revisions of criteria for chronic daily headache. Cephalalgia 2002;22:432-438.
Bigalke H., et al., Botulinum A Neurotoxin Inhibits Non-Cholinergic Synaptic Transmission in Mouse Spinal Cord Neurons in Culture, Brain Research 360;318-324:1985.
Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244-251:1981.
Binder WJ, Brim MF, Blitzer A. Botulinum toxin type A (BOTOX) for treatment of migraine headaches: an open-label study. Otolaryngol Head Neck Surg 2000;123(6):669-676.
Binz T. et al., The Complete Sequence of Botulinum Neurotoxin Type A and Comparison with Other Clostridial Neurotoxins, J Biological Chemistry 265(16);9153-9158:1990.
Blugerman G., et al., Multiple eccrine hidrocystomas: A new therapeutic option with Botulinum toxin, Dermatol Surg May 2003;29(5):557-559.
Blumenfeld AM, Dodick OW, Silberstein SD. Botulinum neurotoxin for the treatment of migraine and other primary headache disorders. Dermatol Clin 2004;22:167-175.
Blumenfeld AM. Botulinum toxin type A as an effective prophylactic treatment in primary headache disorders. Headache 2003;43:853-860.
BOTOX® (package insert). Irvine, California: Allergan Inc; 2004.
Brandes JL, Saper JR, Diamond M, et al. Topiramate for migraine prevention: a randomized controlled trial. JAMA;2004;291:965-973.
Brem, H.; et al, Placebo-Controlled Trial of Safety and Efficacy of Intraoperative Controlled Delivery by Biodegradable Polymers of Chemotherapy for Recurrent Gliomas, Lancet 345;1008-1012:1995.
Brin et al., Report of the Therapeutics and Technology Assessment Subcommittee of the American Academy of Neurology, Neurology, 40:1332-1336, 1990.
Brin MF, Fahn S, Moskowitz C, et al. Localized injections of Botulinum toxin for the treatment of focal dystonia and hemifacial spasm. Movement Dis 1 987;2:237-254.
Brin MF, Swope DM, O'Brien C, et al. BOTOX® for migraine: double-blind, placebo-controlled, region-specific evaluation. Cephalalgia 2000;20:421-422.
Brin, M., et al., Botulinum toxin type A: pharmacology, in Mayer N., editor, Spasticity: etiology, evaluation, management and the role of Botulinum toxin, 2002; pp. 110-124, at 112-113.
Bushara K., Botulinum toxin and rhinorrhea, Otolaryngol Head Neck Surg 1996:114(3):507.
Cao, Y., et al. Functional MRI of chronic daily headache. Cephalalgia 1999;19:462-463.
Castillo JP, Munoz P, Guitera V, et al. Epidemiology of chronic daily headache in the general population. Headache 1999;39:190-196.
Cheshire WP, Abashian SW, Mann JD. Botulinum toxin in the treatment of myofascial pain syndrome. Pain 1994;59:65-69.
Colas R, Munoz P, Temprano R, et al. Chronic daily headache with analgesic overuse: epidemiology and impact on quality of life. Neurology 2004;62:1338-1342.
Couch JR. Placebo effect and clinical trials in migraine therapy. Meth Prob Migraine Trials, Neuroepid 1987:6:178-185.

Cui M, Khanijou S, Rubino J, et al. Subcutaneous administration of Botulinum toxin A reduces formalin-induced pain. Pain 2004;107:125-133.
Cui, M., et al., Mechanisms of the antinociceptive effect of subcutaneous BOTOX®: inhibition of peripheral and central nociceptive processing, Naunyn Schmiedebergs Arch Pharmacol 2002; 365 (supp 2): R17.
Dabrowski et al.; Botulinum toxin as a novel treatment for self mutilation in Lesch-Nyhan syndrome, Ann Neurol Sep. 2002;52(3 Supp 1):S157.
DasGupta et al., Biochemie, 71:1193-1200, 1989.
Depakote® ER (package insert). Abbott Laboratories; 2003.
Dowson, A.J., et al., Managing Chronic Headaches in the Clinic, Int J. Clin Pract., Dec. 2004, 58, 12,pp. 1142-1151.
Duggan et al.; A surbey of Botulinum neurotoxin substrate expression in cells; Mov Disord, 10(3):376: 1995.
Durham PL, Cady Ryan, Cady Roger. Regulation of calcitonin gene-related peptide secretion from trigeminal nerve cells by Botulinum toxin type A: implications for migraine therapy. Headache 2004;44:35-42.
European Agency for the Evaluation of Medicinal Products. Note for guidance on clinical investigation of medicinal products for the treatment of migraine. Dec. 2003.
Fedinic et al., Boll. 1st. Sieroter Milan, 64: 35-41, 1985.
Foster L, Clapp L, Erickson M, Jabbari B. Botulinum toxin A and chronic low back pain. A randomized, double-blind study. Neurol 2001 ;56:1290-1293.
Freund BJ, Schwartz M. Use of Botulinum toxin in chronic whiplash-associated disorder. Clin J Pain 2002;18(6 Suppl):S163-S168.
Fung L. K. et al., Pharmacokinetics of interstitial Delivery of Carmustine 4-Hydroperoxycyclophosphamide and Paclitaxel From a Biodegradable Polymer Implant in the Monkey Brain, Cancer Research 58;672-684: 1998.
Gawade et al., Brain Res., 334:139-146, 1985.
Gladstone JP., Gawel M. Newer formulations of the triptans: advances in migraine management, Drugs. 2003:63(21):2285-305.
Gladstone, J., et al., Chronic Daily Headache: A Rational Approach to a Challenging Problem, Seminars in Neurology, 2003, vol. 23, No. 3, pp. 265-275.
Goadsby et al., N. Eng. J. Med., 346:257-270, 2004.
Gonelle-Gispert et al.; snap-25a and -25b isoforms are both expressed in insulin-secreting cells and can function in insulin secretion;Biochem J 1;339 (pt 1):159-65:1999.
Guyton A.C. et al., Textbook of Medical Physiology, W.B. Saunders Company 1996, ninth edition; 686-688.
Habermann E., et al., Tetanus Toxin and Botulinum A and C Neurotoxins Inhibit Noradrenaline Release From Cultured Mouse Brain, J Neurochem 51(2);522-527:1988.
Habermann E., Inhibition by Tetanus and Botulinum A Toxin of the release of [3H]Noradrenaline and [3H]GABA From Rat Brain Homogenate, Experientia 44:224-226:1988.
Habermann, I-Labeled Neurotoxin from *Clostridium botulinum* A: Preparation, Binding to Synaptosomes and Ascent to the Spinal Cord; Nauyn-Schmiedeberg's Arch. Pharmacol. 1974; 281, 47-56.
Harrison's Principles of Internal Medicine (1998), edited by Anthony Fauci et at., 14th edition, published by McGraw Hill.
Harshman et at., Infect. Immun., 62:421-425, 1994.
Headache Classification Committee of the International Headache Society. Classification and diagnostic criteria for headache disorders, cranial neuralgias and facial pain. Cephalalgia 1988;8 Suppl 7:1-96.
Headache Classification Subcommittee of the International Headache Society. The international classification of headache disorders, 2nd ed. Cephalalgia 2004;24 Suppl 1:1-151.
Heckmann M., et at., Botulinum toxin type A injection in the treatment of lichen simplex: An open pilot study, J Am Acad Dermatol Apr. 2002;46(4):617-9.
Hering R, Gardiner I, Catarci T, Witmarch T, Steiner T, de Belleroche J. Cellullar adaptation in migraineurs with chronic daily headache. Cephalalgia 1993;13:261-6.
Herold et at., Anesthesiology, 77:507-512, 1992.
Holroyd KA, Stensland M, Lipchik GL, et at. Psychosocial correlates arid impact of chronic tension-type headaches. Headache 2000; 40:3-16.

(56) References Cited

OTHER PUBLICATIONS

International Headache Society committee on Clinical Trials in Migraine. Guidelines controlled trials of drugs in migraine. First edition. Cephalalgia 1991; 11:1-12.
Jacks, L., et al., Idiopathic toe walking: Treatment with Botulinum toxin A injection, Dev Med Child Neurol 2002;44(Suppl 91):6).
Jahanshahi M., et al., Psychological functioning before and after treatment of torticollis with Botulinum toxin, J Neurol Neurosurg Psychiatry 1992; 55(3): 229-231.
Jankovic J. et al., Therapy With Botulinum Toxin, Marcel Dekker, Inc., (1994), pp. 5, 150.
Jost W., Ten years' experience with Botulinum toxin in anal fissure, Int J Colorectal Dis Sep. 2002;17(5):298-302.
Katsambas A., et al., Cutaneous diseases of the foot: Unapproved treatments, Clin Dermatol Nov.-Dec. 2002;20(6):689-699.
Klapper JA, Mathew NT, Klapper A et al. Botulinum toxin type A (BTX-A) for the prophylaxis of chronic daily headache. Cephalalgia 2000;20:292-293.
Li Y, et al., Sensory and motor denervation influences epidermal thickness in rat foot glabrous skin, Exp Neurol 1997;147:452-462 (see p. 459).
Linde M, Limmroth V, Dahlöf C, on behalf of the Headache Masters Programme. Ethical aspects of placebo in migraine research. Cephalalgia 2003;23:491-495.
Linton-Dahlöf, M Linde, Dahlöf C. Withdrawal therapy improves chronic daily headache associated with long-term misuse of headache medication: a retrospective study. Cephalalgia 2000;20:658-662.
Lipton RB, Bigal ME. Chronic daily headache: is analgesic overuse a cause or a consequence? Neurology 2003;61 :154-155.
Lipton RB, Stewart WF. Migraine headaches: epidemiology and comorbidity. Clin Neuroscience 1998:5:2-9.
Loder, E., et al., Use of Botulinum Toxins for Chronic Headaches: A Focused Review, The Clinical Journal of Pain, 2002, 18, pp. S169-S176.
Maizels, M., et al., The Patient with Daily Headaches, American Family Physician, Dec. 2004, vol. 70, No. 12, pp. 2299-2306.
Manzoni GC, Granella F, Sandrini G, et al. Classification of chronic daily headache by International Headache Society criteria: limits and new proposals. Cephalalgia 1995:15:37-43.
Marjama-Lyons, J., et al., Tremor-Predominant Parkinson's Disease, Drugs & Aging 16(4);273-278:2000.
Mathew N, Kaup A, Kailasam J. Botulinum toxin type A modifies chronic migraine further long-term (3years) experience with up to ten sets of treatments. Headache 2003:43:576.
Mathew NT, Reuveni U, Perez F. Transformed or evolutive migraine Headache 1987;27:102-106.
Mauskop A. Botulinum toxin in the treatment of chronic daily headaches. Cephalalgia 1999;19:453.
Monzon MJ, Lainez MJA. Quality of life in migraine and chronic daily headache patients. Cephalalgia 1998;18:638-643.
Moyer E et al., Botulinum Toxin Type B: Experimental and Clinical Experience, being chapter 6, pp. 71-85 of "Therapy With Botulinum Toxin", edited by Jankovic, J. et al. (1994), Marcel Dekker, Inc.
Murry T., et al., Spasmodic dysphonia; emotional status and Botulinum toxin treatment, Arch Otolaryngol Mar. 1994; 120(3): 310-316.
Naumann et al; Botulinum toxin type A in the treatment of focal, axillary and palmar Hyperhydrosis and other hyperhidrotic conditions: European J. Neurology 6 (Supp 4): S111-S115:1999.
O'Brien PC, Fleming TR. A multiple testing procedure for clinical trials. Biometrics 1979:35:549-556.
Ondo WG, Vuong KD, Derman HS. Botulinum toxin A for chronic daily headache: a randomized, placebo-controlled, parallel design study. Cephalalgia 2004;24:60-5.
Payne M., et al, Botulinum toxin as a novel treatment for self mutilation in Lesch-Nyhan syndrome, Ann Neurol Sep. 2002;52(3 Supp 1):5157.
Pearce, L.B., Pharmacologic Characterization of Botulinum Toxin for Basic Science and Medicine, Toxicon 35(9);1373-1412 at 1393.

Purkiss J, Welch M, Doward S, et al. Capsaicin-stimulated release of substance P from cultured dorsal root ganglion neurons: involvement of two distinct mechanisms. Biochem Pharmacol 2000;59:1403-1406.
Rabasseda et al., Toxicon, 26:329-326, 1988.
Ragona et al.; Management of Parotid Sialocele With Botulinum Toxin; The Laryngoscope 109:1344-1346:1999.
Rahimtoola H, Buurma H, Tijssen CC, et al. Migraine prophylactic medication usage patterns in The Netherlands. Cephalalgia 2003;23:293-301.
Relja G, Granato A, Maria Antonello R, Zorzon M. Headache induced by chronic substance use: analysis of medication overused and minimum dose required to induce headache, Headache. Feb. 2004;44(2):148-153.
Rogers J., et al., Injections of Botulinum toxin A in foot dystonia, Neurology Apr. 1993;43(4 Suppl2).
Sanchez-Prieto, J., et al., Botulinum Toxin A Blocks Glutamate Exocytosis From Guinea Pig Cerebral Cortical Synaptosomes, Eur J. Biochem 165:675-681:1987.
Saper JR, Lake AE III, Cantrell DT, et al. Chronic daily headache prophylaxis with tizanidine: a double-blind, placebo-controlled, multicenter outcome study. Headache 2002;42:470-482.
Schantz, E.J., et al, Properties and use of Botulinum toxin and Other Microbial Neurotoxins in Medicine, Microbial Rev. 56;80-99:1992.
Scher AI, Stewart WF, Liberman J, et al. Prevalence of frequent headache in a population sample. Headache 1998;38:497-506.
Schim, J, et al., Effect of Preventive Treatment with Botulinum Toxin Type A on Acute Headache Medication Usage in Migraine Patients, Current Medical Research Opinions, vol. 20, No. 1, 2004, pp. 49-53.
Schwartz BS, Stewart WF, Lipton RB. Loss of workdays and decreased work effectiveness associated with headache in the workplace. J Occup Environ Med 1997:39:320-327.
Sevim, S., et al., Botulinum toxin-A therapy for palmar and plantar Hyperhydrosis, Acta Neurol Belg Dec. 2002;102(4):167-170.
Shaari, et al., Otolaryngology—Head and Neck Surgery 112, 566-571 (1995).
Siegel S. Non-parametric statistics for the behavioral sciences. New York: McGraw-Hill Book Company, 1956:96:116-127.
Silberstein SD, Lipton RB, Sliwinski M. Classification of daily and near-daily headaches: field trial of revised IHS criteria. Neurology 1996:47:871-875.
Silberstein SD, Lipton RB, Solomon S, Mathew NT. Classification of daily and near-daily headaches: proposed revisions to the IHS criteria. Headache 1994;34:1-7.
Silberstein SD, Lipton RB. Chronic daily headache, including transformed migraine, chronic tension-type headache, and medication overuse. In: Silberstein SD, Lipton RB, Dalessio DJ, eds. Wolff's headache and other head pain, 7th ed. New York, NY: Oxford University Press;2001 :247-282.
Silberstein SD, Lipton RB. Chronic daily headache. Curr Opin Neurol 2000;13:277-283.
Silberstein SD, Neto W, Schmitt J, et al. Topiramate in migraine prevention. Arch Neurol 2004;61 :490-495.
Silberstein SD, Silberstein MM. New concepts in the pathogenesis of headache. Part II. Pain Man 1990;3:334-342.
Silvestrini M, Bartolini M, Coccia M, et al. Topiramate in the treatment of chronic migraine. Cephalalgia 2003;23:820-824.
Singh, Critical Aspects of Bacterial Protein Toxins, pp. 63-84 (chapter 4) of Natural Toxins II, edited by B.R. Singh et al., Plenum Press, New York (1996).
Sloop RR, Cole BA, Escutin RO. Reconstituted Botulinum toxin type A does not lose potency in humans if it is refrozen or refrigerated for 2 weeks before use. Neurology. Jan. 1997;48(1):249-53.
Smuts JA, Baker MK, Smuts HM, et al. Prophylactic treatment of chronic tension-type headache using Botulinum toxin type A. Eur J Neurol 1999;6(Suppl 4):599-5102.
Solomon GD, Sokbieranda FG, Genzen JR. Quality of life assessment among migraine patients treated with Sumatriptan. Headache 1995;35:449-454.
Spira PJ, Beran RG. Gabapentin in the prophylaxis of chronic daily headache: a randomized, placebo-controlled study. Neurology 2003;61 :1753-1759.

(56) References Cited

OTHER PUBLICATIONS

Stewart WF, Lipton RB, Celentano DD, et al. Prevalence of migraine headaches in the United States. Relation to age, income, race and other sociodemographic factors. JAMA 1992;267:64-69.

Suputtitada, A., Local Botulinum toxin type A injections in the treatment of spastic toes, Am J Phys Med Rehabil Oct. 2002;81(10):770-5.

Tepper and Dodick, Debate: Analgesic overuse is a cause, not a consequence, of chronic daily headache, Headache, 2002; 42:543-554.

Tepper, S., et al., Botulinum Toxin Type A in the Preventive Treatment of Refractory Headaches—Comparison Between Medication Overusers and Nonmedication Overusers Groups, Cephalalgia, 2003, 23, p. 715, poster P5N86.

Troost BT. Botulinum toxin type A (Botox) in the treatment of migraine and other headaches. Expert Rev Neurotherap 2004:4:27-31.

Wang SJ, Fuh JI, Lu SR. et al. Chronic daily headache in Chinese elderly: prevalence, risk factors and biannual follow-up. Neurology 2000;54:314-319.

Wang SJ, Fuh JI, Lu SR. et al. Quality of life differs among headache diagnoses: analysis of SF-36 survey in 901 headache patients. Pain 2001;89:285-292.

Weigand et al.; I-Labelled Botulinum A Neurotoxin: Pharmacokinetics in Cats after Intramuscular Injection; Naunyn-Schmiedeberg's Arch. Pharmacol. 1976; 292, 161-165.

Welch KM. Goadsby PJ. Chronic daily headache: nosology and pathophysiology. Curr Opin Neurol 2002:15:287-95. Review.

Wissel J, Muller J, Dressnandt J, Heinen F, Naumann M, Topka H, Poewe W. Management of spasticity associated pain with Botulinum toxin A. J Pain Symptom Manage 2000;20:44-9.

Woolf C. et al., Neuropathic Pain: Aetiology, Symptoms, Mechanisms, and Management, Lancet 1999; 353:1959-64.

\* cited by examiner

TARGETED DELIVERY OF BOTULINUM TOXIN FOR THE TREATMENT AND PREVENTION OF TRIGEMINAL AUTONOMIC CEPHALGIAS, MIGRAINE AND VASCULAR CONDITIONS

CROSS-REFERENCE TO RELATED APPLICATIONS

This application is a continuation of U.S. application Ser. No. 12/642,545, filed Dec. 18, 2009, now U.S. Pat. No. 8,241, 641, incorporated herein by reference in its entirety, which is a continuation of U.S. Pat. No. 7,655,244, incorporated herein by reference in its entirety, which claims the benefit of U.S. Provisional Application No. 60/593,641, filed Feb. 1, 2005 and which is also incorporated herein by reference in its entirety.

BACKGROUND OF THE INVENTION

Migraine is a primary headache disorder that may be characterized by unilateral throbbing pain which worsens with head movement. This can be associated with other symptoms including nausea, light and noise sensitivity, lacrimation, nasal congestion, and rhinorrhea. An array of factors can trigger migraine headache, such as internal changes (hormonal changes, stress, sleep deprivation) or external changes (weather changes, alcohol, flickering light).

In some cases, a migraine attack begins with a premonitory visual aura. These patients experience a visual disturbance in the form of a zigzag spectrum around a blind spot, which grows in size over a 20-30 min period. This visual effect is known as the "fortification spectrum." The development of the fortification spectrum over time has been shown to correspond to a wave of depression in the activity of cortical neurons, which typically begins in the occipital lobe, and spreads anteriorly. The establishment of this correspondence has permitted the elaboration of a theory about the pathophysiological changes that may cause migraine and other headaches.

As neurons depress, they release nitric oxide (NO), which triggers the dilation of meningeal blood vessels. This vasodilation can result in 3: dull headache, which corresponds to the earliest phase of migraine.

The dilation of the meningeal blood vessels increases the activity of the nerve endings of the primary afferent neurons of the trigeminal nerve that are wrapped around them. As a result, the trigeminal cells release calcitonin gene related protein (CGRP), a vasodilator neuropeptide which further increases the dilation of the meningeal blood vessels, and further feeds into the trigeminal nerve activation. The local intracranial increased activation of the trigeminal nerve spreads through the trigeminal ganglion into the Trigeminal Nucleus Caudalis (TNC) in the brainstem in a process known as peripheral sensitization. The activation of the TNC leads in turn to a central activation process, through its thalamic and cortical projections, which are illustrated in FIG. 1.

Although the pain associated with migraine involves input from meningeal arteries, activation of the TNC may result in referred pain anywhere along the trigeminal network, including the temporal arteries and temporal muscles. The trigeminocervical network involved in the pathophysiology of migraine contains the three main branches of the trigeminal nerve: the ophthalmic branch (V1), the maxillary branch (V2), and the mandibular branch (V3), as illustrated in FIG. 2; as well as the sensory nerves for the posterior head and neck (C2, C3, C4, C5) that feed into the TNC. A detailed anatomical map of the relevant pathways can be found in pages 316, 317, 600, 601 and 736 of Agur, A. M. R. and Dalley II, A. F. (2005) *Atlas of Anatomy* 11$^{th}$ Ed., Lippincott Williams & Wilkins, Philadelphia, which is hereby incorporated by reference.

The activation of the TNC in the brainstem can further spread to the occipital nerve by virtue of its anatomical connection to the TNC, leading to pain sensation in the occipital area. The activation of the TNC can also spread to the parasympathetic system, by activation of a nearby nucleus in the brainstem, the Superior Salivatory Nucleus (SSN), which is connected to the nucleus caudalis through a network of interneurons, as shown in FIG. 3.

Neurons from the SSN synapse with the Sphenopalatine ganglion, which provides vasomotor innervation to blood vessels and secretomotor innervation to the lacrimal glands, nasal and sinus mucosa. When the parasympathetic system is activated, the upper respiratory tract symptoms associated with migraine occur including, potentially, nasal symptoms (rhinorrhea, and post nasal drip), ocular symptoms (conjunctival injection, and tearing) and sinus congestion (pain or pressure around the sinuses). Other parasympathetic projections further aggravate the cascade of events, like the Sphenopalatine ganglion afferents that innervate the meningeal blood vessels. Activation of the parasympathetic system during a migraine attack is also accompanied by a significant increase in the levels of Vasoactive Intestinal Polypeptide (VIP), a parasympathetic neurotransmitter which causes vasodilation and can be measured in high concentrations during a migraine in the jugular venous drainage.

The increased activity of the trigeminal, occipital and parasympathetic systems just described is common to the so-called Trigeminal Autonomic Cephalgias (T AC), which include Cluster headache, Paroxysmal Hemicrania, SUNCT Syndrome, and Hemicrania Continua. Cluster headaches are a primary headache disorder involving attacks of less than 3 hours of duration with severe unilateral peri-orbital and temporal pain. These headaches can be associated with lacrimation, nasal congestion, rhinorrhea, conjunctival injection and a Horner's syndrome. The attacks occur in distinct clusters. Cluster headaches typically involve a series of disabling attacks on a daily basis lasting for months at a time. This pattern recurs annually or biannually.

Paroxysmal hemicrania is a primary headache disorder involving frequent attacks of unilateral, peri-orbital and temporal pain typically lasting less than 30 minutes. The pain can be associated with conjunctival injection, lacrimation, nasal congestion, rhinorrhea, ptosis and eyelid edema.

SUNCT Syndrome is a primary headache disorder characterized by multiple attacks of unilateral, peri-orbital and temporal pain typically lasting less than 2 minutes. The pain is associated with conjunctival injection, lacrimation, nasal congestion, rhinorrhea, and eyelid edema. This headache may be associated with trigeminal neuralgia.

Hemicrania Continua is a primary headache disorder characterized by a strictly unilateral headache responsive to Indomethacin. The pain is associated with conjunctival injection, lacrimation, nasal congestion, rhinorrhea, ptosis, and eyelid edema.

The trigeminal nerve is involved in the pain sensations for all of these headache types, as well as headaches triggered by other pathologies. For example, Temporal Arteritis involves inflammation of the temporal artery with painful palpable nodules along the artery. In addition to headache in the temporal area, Temporal Arteritis causes vision loss and jaw pain.

Headaches can also be associated with ischemic stroke. In a stroke, a lack of blood supply to brain tissue causes a sudden localized neurological deficit. In a large number of affected patients, occlusion of the arteries is due to the presence of atherosclerotic plaques in the arteries supplying the brain, for example, the carotid artery and the vertebral basilar artery. The atherosclerotic plaques are often associated with inflammation which further contributes to occlusion of the blood vessel.

Nociceptive fibers stimulated by inflammatory mediators in infectious or allergic rhinitis can also activate the trigeminal brainstem nucleus and precipitate migraine.

TAC and Migraine are difficult to treat. Numerous medications have been used to prevent Cluster and Migraine headaches from occurring, which include, amongst others: Propranolol, Timolol, Divalproex Sodium, Topiramate, Verapamil, Indomethacin and Amitriptyline. These medicines have numerous side effects and patients are poorly compliant with them. In the case of T AC, Indomethacin, in particular, is difficult for patients to tolerate due to gastrointestinal upset.

All of the headache disorders described above produce disability and better treatment modalities are needed.

Recently, Botulinum toxin has been shown to be effective to treat migraine headaches when injected in the face, cranium and neck (Binder, U.S. Pat. No. 5,714,468). Botulinum toxin is a potent polypeptide neurotoxin produced by the gram positive bacterium *Clostridium botulinum* which causes a paralytic illness in humans termed Botulism. Botulinum toxin has a light and a heavy chain. The heavy chain attaches to a cell surface receptor and the complex is then endocytosed. After endocytosis, the light chain translocates from the endosome into the cytoplasm, where it cleaves a segment of the SNARE protein complex responsible for vesicle fusion in the presynaptic nerve terminal. As a result, the release of neurotransmitters from these vesicles is effectively blocked for 3-6 months.

There are 7 immunologically distinct toxins: A, B, $C_1$, D, E, F and G (Simpson, et al., Pharmacol. Rev., 33:155-188, 1981). These toxins bind to presynaptic membranes of target nerves and appear to work in a similar fashion (Brin, et al., "Report of the Therapeutics and Technology Assessment Subcommittee of the American Academy of Neurology", Neurology, 40:1332-1336, 1990). Botulinum toxin shows a high affinity for cholinergic neurons. Botulinum toxin A produces a reversible, flaccid paralysis of mammalian skeletal muscle, presumably by blocking the exocytosis of acetylcholine at peripheral, presynaptic cholinergic receptors (Rabasseda, et al., Toxicon, 26:329-326, 1988). However, flaccid muscular paralysis is not necessary to achieve the reduction or prevention of migraine symptomatology. In fact, headache pain reduction may be observed at dosages of presynaptic neurotoxin which are lower or higher than dosages required to produce flaccid paralysis of skeletal muscle and without introduction of the neurotoxin into muscle tissue (Binder, U.S. Pat. No. 5,714,468).

Although the molecular basis for the sensation of migraine pain is not clear (Goadsby, et al., N. Eng. J. Med., 346:257-270, 2004), Botulinum toxin might exert its analgesic effect by blocking the release of nociceptive and inflammatory agents that are released during migraine, and not by blocking the release of acetylcholine. Because Botulinum toxin does not act on acetylcholine directly, but on the SNARE protein complex that mediates vesicle fusion, the release of other molecules which is also mediated by the SNARE protein complex is also affected by the toxin (Aoki, Current Medicinal Chemistry, 11:3085-3092, 2004). In fact, studies have shown that Botulinum toxin can also block the release of substance P, which is associated with neurogenic inflammation and pain generation (Aoki, Current Medicinal Chemistry, 11:3085-3092, 2004), glutamate, also associated with nociception (Cui, et al., Pain, 107:125-133, 2004), epinephrine, norepinephrine, and calcitonin gene-related peptide (Aoki, Current Medicinal Chemistry, 11:3085-3092, 2004). Botulinum toxin A does not appear to cause degeneration of nervous or muscular tissue and has been approved for use in certain therapies by the U.S. Food and Drug Administration.

In addition to Botulinum toxin A, other presynaptic neurotoxins have also been suggested to be useful for the treatment of migraine, given the functional characteristics they share with Botulinum toxin (Binder, U.S. Pat. No. 5,714, 468). One of these presynaptic neurotoxins is Tetanus neurotoxin, which is produced by *Clostridium tetani* (DasGupta, et al., Biochemie, 71:1193-1200, 1989), and shows significant sequence homology with serotypes A and E of Botulinum toxin. In particular, fragment The of the Tetanus toxin, which is obtained by peptide digestion of the toxin, appears to act peripherally to produce flaccid paralysis (Fedinic, et al., Boll. 1st. Sieroter Milan, 64: 35-41, 1985; and, Gawade, et al., Brain Res., 334:139-46, 1985).

Staphylococcal alpha-toxin has also been suggested for therapeutic use. This toxin stimulates the production in the brain of muscle-relaxing factor (MRF), which results in reversible, flaccid paralysis of skeletal muscle (Harshman, et al., Infect. Immun., 62:421-425, 1994). Staphylococcal alpha-toxin may function similarly to Botulinum toxin. Other toxins which cause reversible, flaccid paralysis are the acylpolyamine toxins, which are anticholinergic, presynaptic neurotoxins produced in the venom of many invertebrates (Herold, et al., Anesthesiology, 77:507-512, 1992). For example, toxins AR636 and AG489 from spiders *Argiope aurantia* and *Agelenopsis aperta* lead to motor inhibition at a dosage of 2 micrograms and sensory inhibition at 7 micrograms.

Since the use of presynaptic neurotoxins to treat migraines was initially implemented by administering the toxins in the face; cranium and/or neck (Binder, U.S. Pat. No. 5,714,468), the hypothesis about the physiological changes underlying migraine has been significantly developed. The present invention provides an improvement in the therapeutic and preventive use of Botulinum toxin, among other presynaptic neurotoxins, to treat migraines, T AC and other headaches associated with vascular conditions by using a new method to administer these neurotoxins. The improvement is based on the recent theory that has emerged about the pathophysiological changes triggering these headaches, which involves the trigeminal, occipital and parasympathetic systems and therefore affects the administration sites of the toxins.

SUMMARY OF THE INVENTION

There is a need in the medical field to provide an effective therapeutic and prophylactic treatment for migraines, T AC, and other headaches associated with vascular conditions. The invention provides a method for reducing or preventing symptoms and in particular pain related to migraines, T AC, and other headaches associated with vascular conditions in mammals, particularly humans. Specifically, the invention provides an improvement for current methods to treat and prevent these headaches with presynaptic neurotoxins. More specifically, the present invention relates to administering a therapeutically effective amount of a pharmaceutically safe presynaptic neurotoxin, peripherally, along the extracranial trigeminal nerve endings in the temporal region, the extracranial occipital nerve endings in the occipital region, as well as along the intranasal trigeminal nerve endings and parasympathetic nerve endings in the nasal mucosa of a mammal.

The presynaptic neurotoxins of the invention will be those presynaptic neurotoxins that produce reversible, localized paralysis of musculature when administered to a mammal (although to practice the invention such paralysis is not needed) and do not cause degeneration of muscle or nervous tissue. Botulinum toxin, and in particular, Botulinum toxin A is a preferred presynaptic neurotoxin of the invention.

BRIEF DESCRIPTION OF THE DRAWINGS

FIG. 4 has been adapted from Agur, A. M. R. and Dalley II, A. F. (2005) *Atlas of Anatomy* 11$^{th}$ Ed., Lippincottt Williams &Wilkins, Philadelphia. Refer to pages 316, 317, 600, 601 and 736 of the original reference for a detailed view of the anatomy.

DETAILED DESCRIPTION OF THE INVENTION

Figure 1:
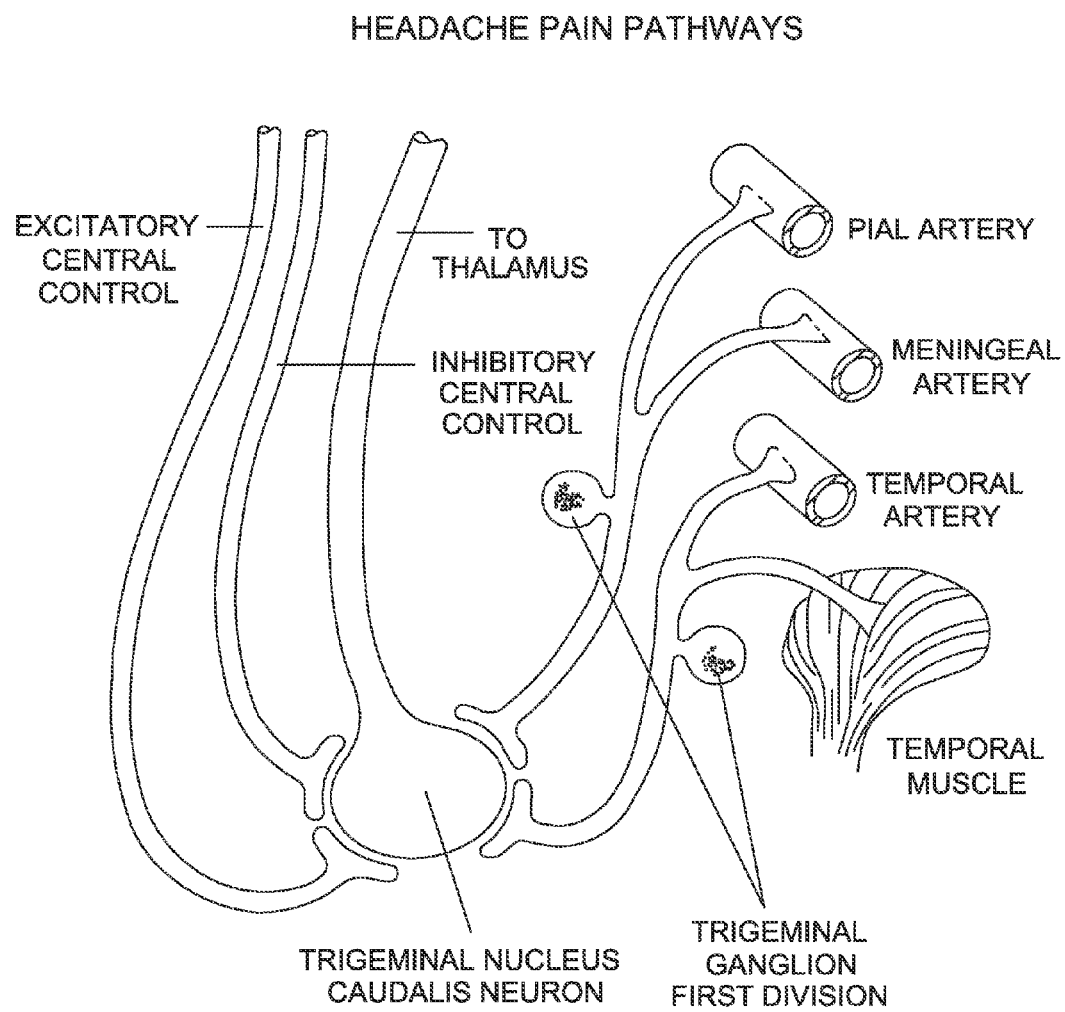
FIG. 1. Diagram of headache pain pathways, illustrating the input and output pathways of the trigeminal nucleus caudalis in the brainstem.
Figure 2:
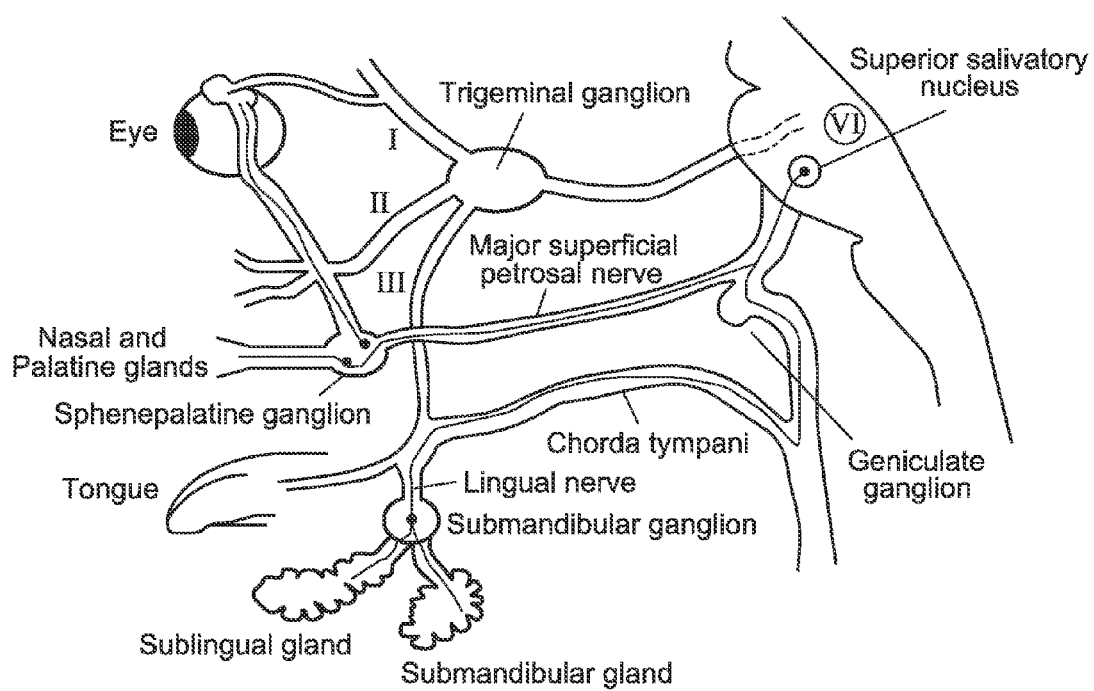
FIG. 2. Diagram of the trigeminal and parasympathetic network involved in headache pain, from and into the brainstem.
Figure 3:
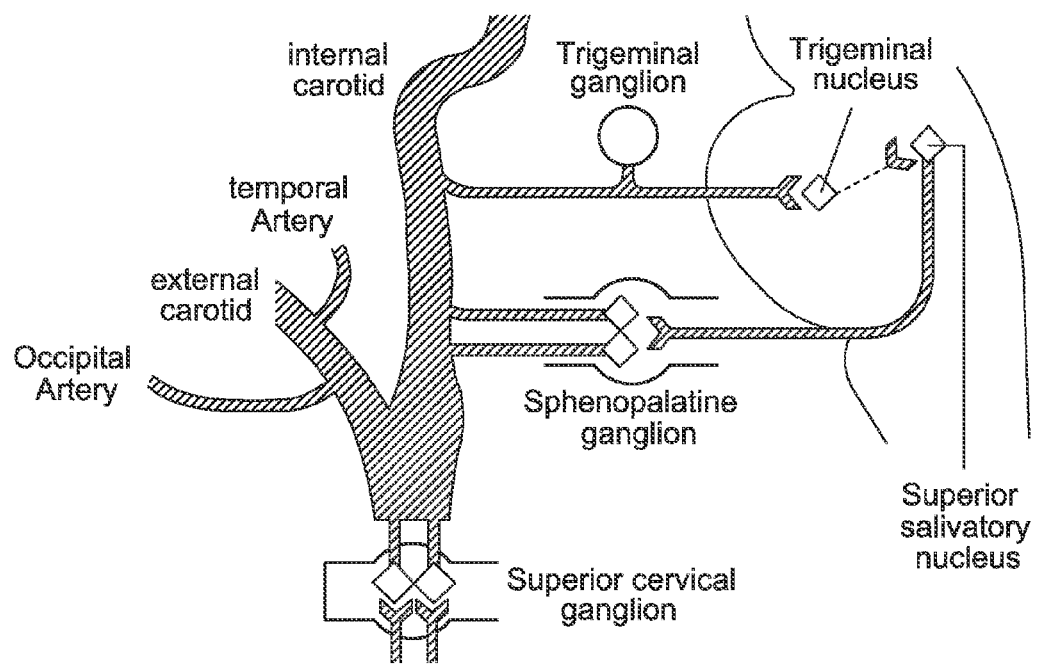
FIG. 3. Diagram of the neural innervation of the cranial circulation, illustrating the trigeminal nociceptive input from the internal carotid to the trigeminal nucleus caudalis of the brainstem, and the connection to the parasympathetic system through the superior salivatory nucleus. The parasympathetic system feeds back into the internal and external carotids, which connect with the temporal and occipital arteries.
Figure 4:
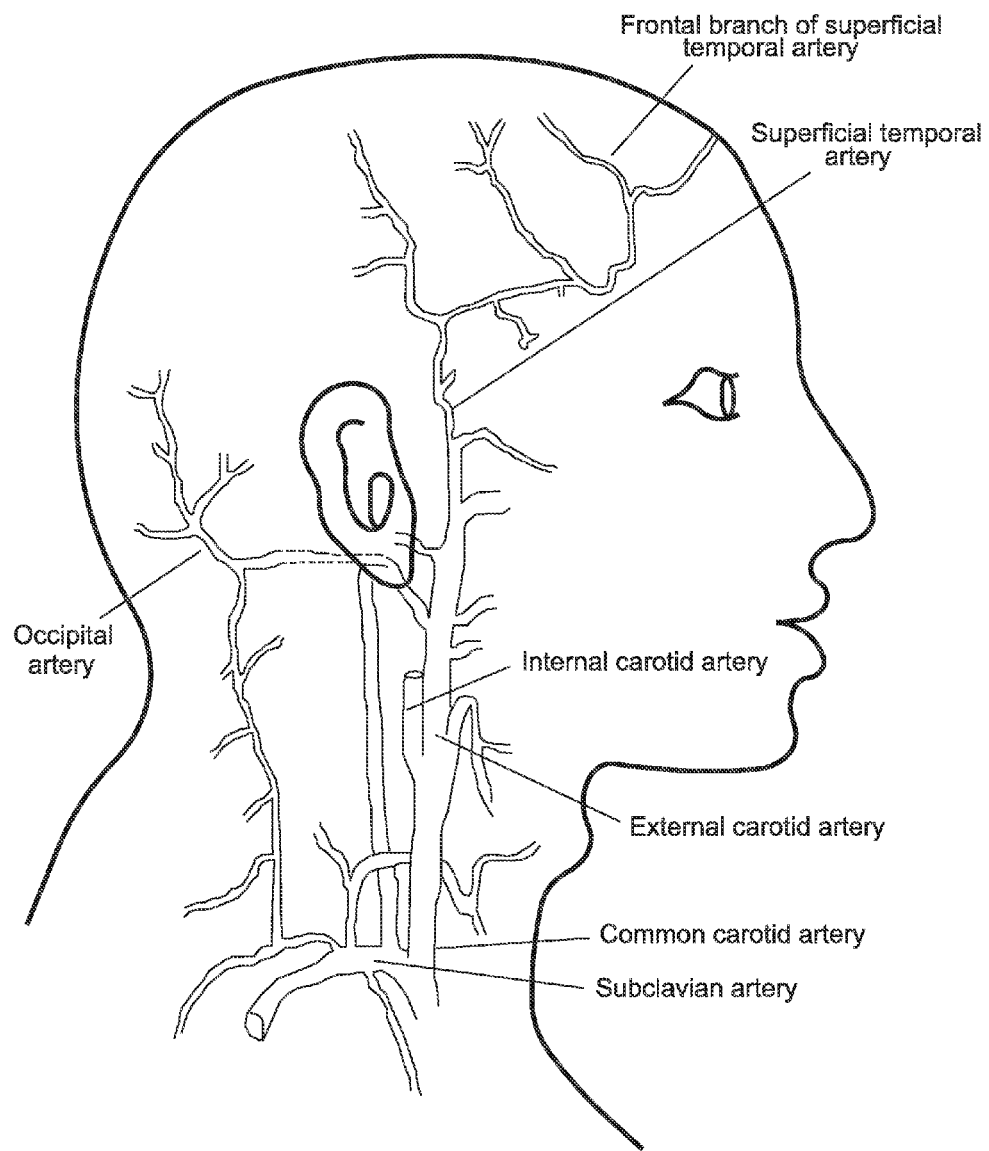
FIG. 4. Illustrated lateral view of a human head showing the connection between the external carotid and the superficial temporal and occipital arteries.

The anatomical and physiological theory of migraine, TAC, and other headaches associated with vascular conditions, as described in the Background section, suggests that blockade of the release of nociceptive and inflammatory agents triggered by the hyperactivation of the trigeminal, occipital and parasympathetic systems involved in the development of these headaches should provide an effective therapeutic and/or prophylactic treatment. As FIGS. 1 and 2 show, some of the anatomical pathways involved in the development of these headaches are intracranial; therefore, specific blockade of the intracranial pathways involved by noninvasive means is not feasible. However, some of the pathways affected are located extracranially under the surface of the skin or intranasally, and are therefore accessible to treatment. Some examples of these pathways include the temporal arteries and muscles (FIGS. 1 and 4), the nasal glands and mucosa (FIG. 2) and the occipital nerve and artery (FIG. 4). The current invention relates to providing a method for blocking the release of nociceptive and inflammatory agents triggered by the hyperactivation of the trigeminal, occipital and parasympathetic fibers that is increased during migraine, TAC or other headaches associated with vascular conditions.

The therapeutic modality used to treat and/or prevent the conditions described in this patent is the use of presynaptic neurotoxins. "Presynaptic neurotoxin" as used in this disclosure refers to those neurotoxins and their derivatives which are known to produce localized, reversible flaccid paralysis of musculature in mammals which does not result in degeneration of muscle or nervous tissue. However, as stated earlier, flaccid muscular paralysis which the presynaptic neurotoxins of the invention will produce is not necessary to achieve the reduction or prevention of headache symptomatology with the method of the invention.

In a preferred embodiment, the presynaptic neurotoxin of the invention is Botulinum toxin. In a particularly preferred embodiment of the invention, the presynaptic neurotoxin is Botulinum toxin A. Botulinum toxin A is presently supplied and commercially available as "Botox"® by Allergan, Inc. of Irvine, Calif., and as "Dysport"® by Ipsen, of Berkshire, UK. In another embodiment of the invention, the presynaptic neurotoxin is Botulinum toxin B. Botulinum toxin B is commercialized as "Neurobloc"®/"Myobloc"® by Solstice Neuroscience, Inc, of San Francisco, Calif. A pentavalent toxoid of all eight known Botulinum serotypes is also available as an investigational drug from the U.S. Center for Disease Control in Atlanta, Ga. The Botulinum A toxin preparations are most preferred for their known safety and efficacy. Botox® has also been used to treat, among other things, cervical dystonia, brow furrows, blepharospasm, strabismus, and hyperhidrosis.

Tetanus toxins are also commercially available for use as vaccines. Since the Ibc fragment of the Tetanus toxin is likely to act in a similar fashion to Botulinum toxin, as suggested earlier, a further embodiment of the invention will preferably comprise the use of pharmaceutically safe forms of the Ibc fragment of the Tetanus toxin rather than the intact form of the toxin.

Obtaining the presynaptic neurotoxins of the invention, including the Botulinum and Tetanus toxins, in a pharmaceutically safe form and therapeutically effective amount should be known or easily determined by those of ordinary skill in the art. The presynaptic neurotoxins should preferably be in a nontetragenic form that does not trigger a detectable immune response. Pharmaceutical safety will be dose-dependent for most of the presynaptic neurotoxins of the invention, in such a way that fairly low doses of toxin will be "safe" as compared to doses known to produce disease.

The presynaptic neurotoxins of the invention will be preferably administered as a composition in a pharmaceutically suitable carrier. For this purpose, presynaptic neurotoxin compositions will be prepared for administration by combining a toxin of the desired degree of purity with physiologically suitable sterile carriers. These carriers will not produce toxic responses in recipients at the doses and concentrations used. In a preferred embodiment, the preparation of such compositions typically involves mixing the presynaptic neurotoxin with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. These compositions can also be lyophilized and will be pharmaceutically acceptable; i.e., appropriately prepared and approved for use in the desired application.

To facilitate administration, the presynaptic neurotoxins will most preferably be formulated in unit dosage form. The presynaptic neurotoxins may be supplied, for example, as a sterile solution or as a lyophilized powder in a vial.

In general, the amount of presynaptic neurotoxins used for treatment will be determined by the age, gender, presenting condition and weight of the patient, in consideration of the potency of the presynaptic neurotoxin. The potency of a toxin is expressed as a multiple of the $LD_{50}$ value for a reference mammal. One "unit" of toxin is the amount of toxin that kills 50% of a group of mammals that were disease-free prior to inoculation with the toxin. For example, one unit of Botulinum toxin is defined as the $LD_{50}$ upon intra peritoneal injection into female Swiss Webster mice weighing 18-20 grams each. One nanogram of the commercially available Botulinum toxin A typically contains about 40 mouse units. The potency in humans of the Botulinum toxin A product currently supplied by Allergan, Inc. as "Botox"® is estimated to be about $LD_{50}$=2,730 units.

Assuming an approximate potency of $LD_{50}$=2,730 units, the presynaptic neurotoxin can be administered in a dose of up to about 1,000 units; however, dosages of as low as about 2.5 to 5 units will have therapeutic efficacy. Dosages between 2.5 or 5 units and as high as 250 units will be normally used, and in a preferred embodiment, individual dosages will be of about 15-30 units. Typically, the presynaptic neurotoxin will be administered as a composition at a dosage that is proportionally equivalent to a range of between 1 cc-5 cc/100 units, which translate to 100 units/cc-20 units/cc. Adjustment of these dosages depending on the greater or lesser potency of the presynaptic neurotoxins and factors identified above should be easily determined by those of ordinary skill in the art.

In the preferred embodiment, the dosage used will be the lowest one which is still therapeutically effective (i.e., the dosage which results in detection by the patient of a reduction in the occurrence and/or magnitude of headache pain experienced by the patient, even though other symptoms associated with the pain, such as the premonitory aura, may persist). The patient's sensitivity to, and tolerance of, the presynaptic neurotoxin can be determined in the initial treatment, by administering a low dosage at one site. Additional administrations of the same or different dosages can be provided as needed.

The injections will be repeated as necessary. As a general guideline, Botulinum toxin A administered into or near muscle tissue has been observed to produce flaccid paralysis at target site muscles for up to about 3 to 6 months. However, increased efficacy of the treatment using Botulinum toxin A is expected to happen when the toxin is administered according to the method of the invention at about 3 month intervals.

In a preferred embodiment of the invention, commercially available Botox® can be reconstituted with sterile non-preserved saline prior to injection. Each vial of Botox® contains 10 about 100 units of *clostridium Botulinum* toxin type A purified neurotoxin complex. Dilutions will vary depending upon the commercial preparation.

The technique of administrating presynaptic neurotoxins to modulate the parasympathetic, trigeminal and occipital nerve responses involved in T AC, migraine and other headaches associated with vascular conditions, involves distributing the presynaptic neurotoxins around the nerve endings involved. Because a high concentration of the trigeminal nerve endings are wrapped around the arteries, injections of presynaptic neurotoxins along the trajectory of the temporal extracranial artery is an effective way of administering presynaptic neurotoxins, and in particular Botulinum toxins, for the treatment of migraine, TAC and other headaches. The same rationale applies to the occipital nerve endings along the extracranial occipital artery. This method helps to locate the synaptic terminals of the targeted nerves, which allows for the maximum adherence of presynaptic neurotoxins to the pain generating nerves involved in headache disorders.

In a preferred embodiment of this invention, the presynaptic neurotoxins are administered by way of injection. However, in other embodiments, the presynaptic neurotoxins may be administered topically. In general, the preparation of the presynaptic neurotoxin solution for topical delivery may be the same as that which is injected. However, in other embodiments, the presynaptic neurotoxin may be applied topically via a carrier known to those of skill in the art. The solutions can then be administered by several means, like for example, a pledget of cotton or cotton tipped applicator, a dropper or a spray in the case of a solution, or a spatula in the case of a cream. These topical methods of application may be used wherever trigeminal, occipital or parasympathetic nerve endings can be accessed efficiently by such application. The solution containing the presynaptic neurotoxins can be administered topically to the epidermis through these means and the presynaptic neurotoxins can then be distributed through the epidermis by transdermal carrier systems. As would be obvious to one of skill in the art, topical administration may not be as effective as administration via injection depending on, for example, the patient, the severity of the symptoms and access to the trigeminal, occipital and parasympathetic nerves.

The target administration sites for the current invention are the extracranial and intranasal trigeminal nerve endings and parasympathetic nerve endings of the nasal mucosa, the extracranial temporal trigeminal endings and the extracranial occipital nerve endings. The parasympathetic nerve endings in the nasal mucosa, also situated around the lacrimal glands are illustrated in FIG. 2. The trigeminal nerve endings are situated around the temporal artery (FIG. 4) and temporal muscle, as shown in FIG. 1, and the occipital nerve endings are located around the occipital arteries (FIG. 4) via cervical nerve roots that connect with the trigeminal spinal nucleus. Presynaptic neurotoxins injected in these locations every 3-6 months produce a therapeutic beneficial effect on migraine, TAC and other headaches associated with vascular conditions.

Nasal Administration

To target the intranasal trigeminal nerve endings and parasympathetic nerve endings in the nasal mucosa, the method of administration involves infiltrating the upper respiratory tract (nasal mucosa and turbinates) with a presynaptic neurotoxin diluted with a suitable solution such as saline. There is a coalescence of nerve fibers within the upper region of the nose (intranasally) near the cribiform plate and above the superior turbinate. It is also known anatomically that the inferior turbinate, which is the most responsive organ in the nose, is formed of bone and mucosa composed of vascular lakes that provide the basis for nasal sprays and topical medications administered intranasally which provide for rapid local transmucosal absorption.

In a preferred embodiment, Botulinum toxin Type A (Botox®) is used, and each nostril is infiltrated with 5 to 10 units using a solution of 100 units of Botox® diluted with 4 cc of normal saline. The infiltration in this preferred embodiment is performed by injection using a 30 gauge needle. Intranasal injections are given in each nostril using endoscopic application, or a needle palpation technique. The needle is inserted through the nostril. Lateral and medial mucosal infiltration is performed either through finger palpation and guidance or through direct visualization using a nasal speculum and an external light source or via endoscopic guidance.

In another embodiment, Botox® is used and it is administered in the region of the external nares using 5 to 10 units using a solution of 100 units of Botox® diluted with 4 cc of normal saline. The infiltration in this preferred embodiment is performed by injection using a 30 gauge needle. If necessary, Botox® can be also administered in the distribution of the infraorbital nerve.

In another embodiment of the invention, infiltration of the presynaptic neurotoxins in the upper respiratory tract will be done by topical administration to the intranasal mucosa (either alone or with a carrier substrate) which, because of its anatomical proximity to the end terminals of the trigeminal nerve or the sphenopalatine ganglion that innervate the nose, will have a direct effect on the alleviation of headache pain. In a particular embodiment, the presynaptic neurotoxin solution, with or without a carrier, will be delivered with a cotton pledget or a dropper and spread along the targeted area. In another embodiment of the invention, the presynaptic neurotoxin solution, with or without a carrier, will be delivered in the form of an emollient, cream or solution, and spread over the epidermis of the targeted area. In yet a different embodiment of the invention, the presynaptic neurotoxin solution, with or without a carrier, will be delivered in the form of a spray. Other embodiments may use alternative methods of topical delivery known to those of skill in the art.

EXAMPLE 1

A 48 yr. old female patient with chronic migraine associated with rhinorrhea and cervical 20 dystonia was treated with the method of the present invention. Her migraines involved the left hemicranium and were associated with left rhinorrhea. Initial Botulinum toxin treatment using migraine and cervical dystonia protocols improved her headaches, but did not completely abort them, while the rhinorrhea persisted. The patient was treated with intranasal injections of Botox® 2.5 units (4 cc dilution) four times on the left side only, using the needle palpation approach. There was no change in the shape of the nose or the cartilage base. The discomfort was minimal and the bleeding was not excessive. Two weeks after the treatment, both the rhinorrhea and the headache were resolved.

Temporal Administration

To target the extracranial trigeminal nerve endings in the temporal region, the extracranial temporal artery is palpated and the skin is marked where the artery's pulsations are felt. The area is then infiltrated with presynaptic neurotoxins diluted in a suitable solution such as normal saline along the course of the artery. In a preferred embodiment, the presynaptic neurotoxin used is Botulinum toxin A, and the total dose given per artery is 20 units using a solution of 100 units of Botox® diluted with 2-4 cc of normal saline. The infiltration in this preferred embodiment is performed by injection with a 30 gauge needle.

In the case of headaches stemming from Temporal Arteritis, presynaptic neurotoxins are infiltrated around the temporal artery using a similar technique to that just described. In a preferred embodiment of the invention, Botulinum toxin will be administered by injection.

In another embodiment of the invention, infiltration of the presynaptic neurotoxins along the temporal artery will be done by topical administration, in a similar way as that described for the intranasal area. In a particular embodiment, the presynaptic neurotoxin solution will contain a transdermal carrier. In a different embodiment, the presynaptic neurotoxin solution will be delivered in the form of a spray along the temporal artery, and care will be taken to shield the non-targeted areas of the scalp.

Occipital Administration

The occipital artery can be treated in a similar fashion. The artery is located using the following landmarks: the midpoint between the nucal ridge (inion) and the mastoid process is found; light palpation is used to feel the occipital artery's pulse. The hair is separated and the skin is marked along the course of the artery. Presynaptic neurotoxins diluted in normal saline or other suitable solution are infiltrated around each artery. In a preferred embodiment, 20 units of Botox® in divided doses are infiltrated around each artery using a solution of 100 units of Botox® diluted with 2-4 cc of normal saline. The infiltration in this preferred embodiment is performed by injection with a 30 gauge needle.

In another embodiment of the invention, infiltration of the presynaptic neurotoxins along the occipital artery will be done by topical administration, in the same way described earlier for the temporal administration.

Depending on the condition of each patient, the presynaptic neurotoxins will be administered to one of the sites just described, or to multiple sites. In one embodiment, there are multiple administration sites. In a particular preferred embodiment, the doses ranging between 25 units and 250 units are equally divided among the different administration sites. One of skill in the art should readily ascertain how to adjust the number of administration sites and dosages based on individual profiles of weight, gender, age, condition severity and symptoms.

Other Administration Sites

In embodiment of the invention, one can utilize a direct sphenopalatine administration of presynaptic neurotoxins, which in a preferred embodiment will be Botulinum toxins, and in particular, Botulinum toxin A. In one embodiment, this treatment may follow prior treatments in which the presynaptic neurotoxin had been administered at any of the foregoing sites without sufficient results.

In the case of atherosclerotic disease, presynaptic neurotoxins, preferably Botulinum toxins can be injected directly into the plaque via an intra-arterial catheter. Botulinum toxins will be of benefit as these plaques produce inflammation in the blood vessel wall in response to cholesterol deposits. This inflammation further compromises the diameter of the lumen of the blood vessel. Botulinum toxins will focally reduce this inflammation for 3 to 6 months.

For the administration of presynaptic neurotoxins by injection, dilution dependent syringes with gauging for units rather than volume injected are recommended. This will ensure that the volume injected contains the desired amount of units, since the volume injected will depend on how the original concentration of the presynaptic neurotoxin was diluted when reconstituted. For example, in the embodiment in which 100 units of Botulinum toxin A are reconstituted in 4 cc of normal saline, a specific syringe with demarcations at 0.1 cc of 2.5 units, and at 0.2 cc of 5 units will be used. In another embodiment in which 100 units of Botulinum toxin A are reconstituted in 1 cc of normal saline, the syringe with demarcations at 0.1 cc of 10 units; and at 0.2 cc of 20 units will be used. These delivery tools allow for accurate delivery and recording of the dose given.

The invention having been fully described, examples illustrating its practice should not, however, be considered to limit the scope of the invention.

What is claimed is:

1. A method for reducing the occurrence and magnitude of headache pain in a mammal, wherein mammal has suffered headache pain associated with a headache from the group consisting of: migraine, trigeminal autonomic cephalgia and headache caused by a vascular condition, comprising administering in a pharmaceutically safe form to a mammal, a therapeutically effective amount of a botulinum neurotoxin type A to nasal parasympathetic nerve endings, thereby reducing the occurrence and magnitude of headache pain in the mammal.

2. The method according to claim 1 wherein the botulinum neurotoxin is administered by injection.

3. The method according to claim 1 wherein the botulinum neurotoxin is a Botulinum toxin complex.

\* \* \* \* \*